United States Patent [19]

Boone

[11] Patent Number: 4,465,064
[45] Date of Patent: Aug. 14, 1984

[54] ORTHOPEDIC DEVICE AND METHOD FOR SUPPORTING AND TREATING PORTIONS OF THE BODY

[76] Inventor: Philip Boone, 15 Fenwick Rd., Winchester, Mass. 01890

[21] Appl. No.: 350,983

[22] Filed: Feb. 22, 1982

[51] Int. Cl.$^3$ ............................................. A61F 5/04
[52] U.S. Cl. .................................. 128/88; 128/89 R
[58] Field of Search ..................... 128/87 R, 88, 89 R, 128/90, 91, 149

[56] References Cited

U.S. PATENT DOCUMENTS

| | | | |
|---|---|---|---|
| 323,775 | 8/1885 | Bender et al. | 128/89 R |
| 2,711,168 | 6/1955 | Brickman et al. | 128/89 R |
| 2,781,757 | 2/1957 | Hauser et al. | 128/89 R |
| 2,933,083 | 4/1960 | Kozdas | 128/89 R |
| 3,097,644 | 7/1963 | Parker | 128/89 R |
| 3,580,248 | 5/1971 | Larson | 128/89 R |
| 3,606,884 | 9/1971 | Peter | 128/149 |
| 3,662,057 | 5/1972 | Webster et al. | 128/89 R |
| 3,998,219 | 12/1976 | Mercer et al. | 128/89 R |
| 4,129,127 | 12/1978 | Ellison | 128/89 R |
| 4,217,893 | 8/1980 | Payton | 128/89 R |
| 4,316,457 | 2/1982 | Liegeois | 128/89 R |

Primary Examiner—C. Fred Rosenbaum
Assistant Examiner—C. W. Shedd

[57] ABSTRACT

A device or assemblage for effecting immobilization, support, healing and repair of body areas such as displaced or injured bone structure. More particularly, the invention relates to an orthopedic device and method which are simpler, faster and more complete than any known means or technique for a related purpose. Of considered prime importance is the fact that the special cast structure of the invention permits direct and immediate access to the affected body area at all times, after the cast is formed, for any purpose such as inspection or treatment.

Contrary to this advantage, conventional plaster cast or known cast forming tapes, wound around an appendage, do not permit such action but require removal of the cast by cutting, a delicate and time-consuming procedure, unpleasant to the subject. The present device eliminates entirely the necessity of cutting the cast for its removal, even after the rehabilitation period. Other structural and functional advantages relate to splint-cast adaptability, an improved healing environment, a choice of cast-forming materials, etc. The term "cast" as used herein is generally intended to cover a splint also and the latter will not be repeated each time.

14 Claims, 13 Drawing Figures

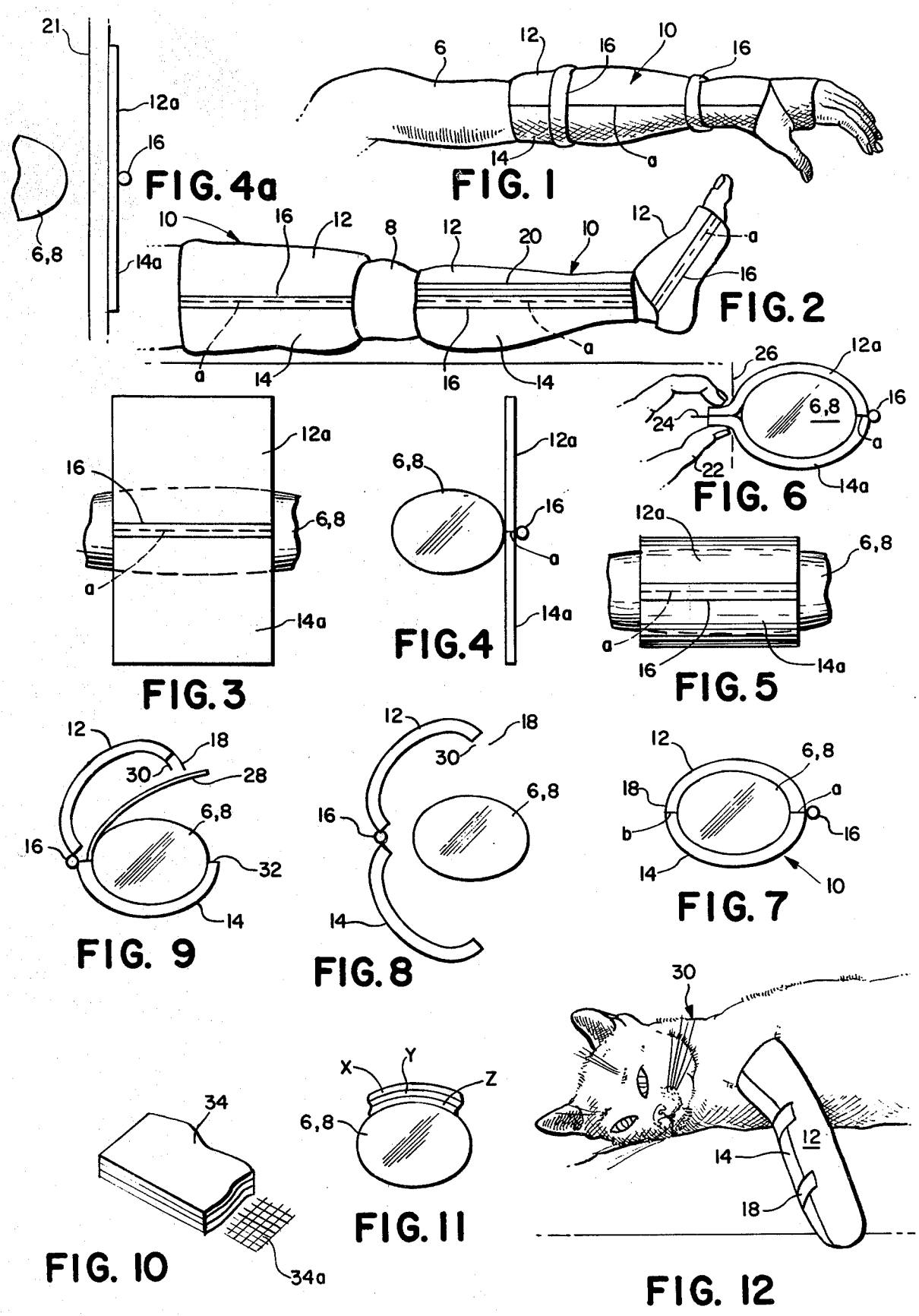

ORTHOPEDIC DEVICE AND METHOD FOR SUPPORTING AND TREATING PORTIONS OF THE BODY

BRIEF SUMMARY OF THE INVENTION

The subject invention broadly relates to a method and an associated apparatus, assemblage or device for orthopedic usage believed to possess distinct advantages over known methods and devices for the purpose. While primarily considered relative to human adaptability, veterinary usage may also appear as benefitting therefrom.

The invention assumes the conventional initial steps of preparation of the affected body area and adjustment or setting of impaired bone structure of the subject as may be necessary. In brief, this is followed by placement of two sheet-like, interconnected, sections of given dimensions and having cast-forming properties on or around the affected area or appendage, such as an arm, leg, neck, etc. The two sections are joined at one contiguous edge of each pivotally or hingedly, as by a flexible adhesive tape, and are adapted to be releasably joined at an opposite contiguous edge of each by another strip of adhesive tape after superimposition on the body area.

At this stage, assuming, for example, the two interconnected sections to have been wrapped around respective halves of an injured appendage to assume a curved disposition, the sections are subjected to a liquid which chemically reacts with cast-forming components thereof to form two completed cast sections enclosing the appendage and held together firmly by the aforesaid adhesive tape. Either section may be opened instantly by peeling back the closure strip of tape, and again closed by reinstalling it. Each of the sections may comprise a plurality of overlaid layers of the cast-forming sheet material for ultimate strength and rigidity of the cast. Variations of the foregoing procedure, e.g. relating to omission of the liquid or timing of its introduction are covered in detail below.

Objects of the invention are to provide an orthopedic device and related method which are simpler and more efficacious than known means or methods for a related purpose; to provide an optional splint-cast adaptation device; to provide a device permitting instant visual and tactile access to a body area underlying a cast for inspection and treatment as required; to provide said visual and tactile access by pivotally movable cast sections; to provide means which avoid the necessity of cutting the cast for its removal; to provide a device as set forth adapted to adjust to body members of various dimensions; to provide an improved healing environment at the affected body area; to provide a device or assemblage producing an improved air circulation at an affected area; to provide a cast permitting a choice of chemical and other materials in its production; and to provide a cast at a time and possible expense advantage. Other objects will be made evident hereinafter.

BRIEF DESCRIPTION OF THE DRAWING

The novel features which are believed to be characteristic of the invention are set forth with particularity in the appended claims. The invention, however, both as to its organization and its method of operation will best be understood from the following description when read in connection with the accompanying drawing wherein like numbers have been employed in the different figures to denote the same parts and wherein:

FIGS. 1 and 2 are side views of an arm and leg, respectively, of a subject under treatment illustrating cast devices of the invention in functional position;

FIG. 3 is a plan view showing preliminary positioning of a two-section cast-producing device relative to an arm of the subject prior to formation of the cast;

FIG. 4 comprises a sectional view of the arm and a side view of the two flexible cast-producing sections of FIG. 3;

FIG. 4a is a side view of the components of FIG. 4 showing a barrier sheet interposed between the cast-producing sections and an arm appendage;

FIG. 5 is a plan view of the two cast-producing sections in functional position, wrapped around the appendage and ready for introduction thereto of an activating liquid which, alternatively, might be introduced at FIG. 3.

FIG. 6 illustrates a step of wrapping the two cast-forming sections firmly around the appendage;

FIG. 7 is a sectional view of the appendage with a completed two-section cast positioned therearound;

FIG. 8 merely represents the ability of either of the completed cast sections to be opened. Both sections would be opened together only for final cast removal;

FIG. 9 shows opening of one completed cast section for inspection and treatment purposes;

FIG. 10 is a fragmentary perspective view of one of the cast-producing sections indicating possible alignment of the pores of the sheet material layers. A fragment of a reinforcing or truss element for incorporation in the section is also shown;

FIG. 11 is a fragmentary sectional view of a body member with a multilayer cast-forming or completed cast positioned thereon; and FIG. 12 is a prespective view of a completed two-section cast as applied to veterinary usage.

DETAILED DESCRIPTION

Referring to FIGS. 1 and 2, respectively, an injured appendage such as an arm 6 and a leg 8 of a subject under treatment are each shown releasably held in a cast device 10 of the invention, comprising the complementary and separable cast sections 12 and 14. The sections 12 and 14 are held closed at contiguous edges "a" by adhesive tape means 16 serving pivotally as a hinge. They are held releasably closed at contiguous edges "b" (not visible in FIGS. 1 and 2 but shown in FIG. 7) by adhesive tape means 18. By removing closure tape means 18 cast sections 12 or 14 are adapted to be pivotally opened by hinge tape means 16 and thereafter closed and so held by tape means 18.

The terminology "cast-producing sections" used repeatedly herein refers to the sections prior to their assuming completed cast form, and the terminology "cast sections " refers to the sections after assuming completed cast form.

In FIGS. 3-6 two cast-producing sections 12a and 14a are shown, namely, those producing the completed cast sections 12 and 14 of FIGS. 1 and 2, supra. In FIGS. 3 and 4 the sections are shown superimposed with the appendages 6 or 8 and flexibly joined at contiguous edges "a" by the hinge-functioning tape 16. In FIG. 4a, a barrier layer 21 is shown, its purpose being to prevent passage of a processing liquid from cast-producing sections 12a and 14a to the appendage or body member (6 or 8). The layer 21 may appropriately be composed of an elastomeric material such as polypropylene or a silicone-treated sheet, assuming, for example, water as a reactive component to be employed. In FIG. 5 the joined cast-producing sections 12a and 14a are shown wrapped around appendage 6 or 8, for instance just prior to completed cast formation, described below.

FIG. 6 illustrates the cast-producing sections 12a and 14a drawn around an appendage 6 or 8. The joined sections slightly exceed the circumference of the appendage. The free ends are grasped by fingers 22 and may be clipped or clamped together, temporarily, by means, not shown. A thin strip of silicone treated release paper 24 may advantageously be inserted between the ends of the sections to prevent their sticking together. A similar strip may also be inserted between the section extremities adjacent to hinge tape 16.

Just before or immediately after completion of the cast-forming process the protruding ends of sections 12a and 14a may be served as at dotted line 26 by shears or the like.

The appendage 6 or 8 is encompassed by the completed cast sections 12 and 14 in FIG. 7. The sections are held firmly in position by the hinge component 16 and the closure adhesive tape 18.

FIG. 8 merely illustrates the propensity of either cast section 12 or 14 to be pivoted to an open position. It is to be understood, however, that both sections would not be moved together to open positions except for complete removal of the cast.

In FIG. 9 opening of one of the sections while the other is closed and holds the appendage against movement is shown. The padding component 28 has also been displaced permitting unobstructed visual and tactile access to the appendage.

A substantial alignment of the pores of a cast-forming material is shown in FIG. 10. This is achieved in a multilayer structure 34 by superimposing sheets of the material in contrast to winding layers of cast-forming tape diagonally around an appendage. Element 34a represents a reinforcing or truss component which may be embedded between given layers of element 34 or bonded to a rear surface thereof to provide additional strength. Element 34a could be formed to the desired contour being composed of metallic or plastic material adapted thereto.

In a preferred embodiment the cast-producing sections 12a and 14a are each composed of one or more superimposed layers of a flexible web or fabric such as a knitted material composed of fiberglass filaments and having marked pores or interstices between filament components to provide substantial porosity conductive to air circulation. The cast-producing sections, as previously described, are superimposed with injured body areas or the like. The material composing the sections has impregnated, coated or otherwise adhesively diffused therewithin a polyurethane resin, e.g. of a non-foaming or low-foaming type. This resin or polyurethane pre-polymer, when subjected to water, reacts therewith and solidifies to form, in conjunction with its carrying material, a rigid sturdy cast, relatively light in weight, of a given porosity and penetrable by x-rays. Prior to hardening, the fabric and carried resin can be manually molded or formed to the contours of the body area.

Again referring to the terminology, the "cast-producing sections" are those prior to introduction of a reactive liquid, water in the present example, and the "cast sections" are those after said introduction and hardening.

Referring particularly to FIGS. 3 and 4, the processing liquid may be introduced to the sections 12a and 14a carrying the polyurethane prepolymer by such procedures as dipping them in water or applying a saturated sponge or brush with pliant bristles thereto.

Other substances and procedures for forming cast components are possibly adaptable to employment with structures of the present invention. In any case, at least one of the substances, e.g., a prepolymer composition must be disposed on or impregnated in a flexible sheet-like support material to which another substance, e.g., a liquid acting as an activator or catalyst is introduced.

Among such substances and methods are:

1. A liquid curable material such as a non-foaming or foaming polyurethane prepolymer composition and a catalyst, self-curing or requiring heat or ultraviolet radiation. The reaction components may be di-isocyanates or polyisocyanates and dipolyols which react to produce a polyurethane resin.

2. A material impregnated with a solution of a thermoplastic resin such as a polycarbonate in a solvent, e.g. methylene chloride. The solvent evaporates leaving the hardened resin.

A fragment of a multilayer structure, somewhat exaggerated as to thickness, is shown in section in FIG. 11. It indicates possible multilayer content and arrangement of materials designated X, Y and Z. Thus layer X may be the completed composite cast 10 of FIGS. 1, 2 and 7–9; layer Y the barrier layer 21 of FIG. 4a, and layer Z the padding layer 28 of FIG. 9. Alternatively, layer X may represent the cast-producing sections 12a and 14a, e.g., the fiberglass support and the polyurethane prepolymer impregnated therein; layer Y a layer of soft, pliant, resilient flocked material adapted to follow the contours of the body area under treatment when pressed thereagainst, and layer Z a preferably elastomeric barrier layer for barring passage of a liquid. Layer Y may, appropriately, also have the polyurethane prepolymer impregnated therein. Materials for possible use in forming the flocked layer Y include fiber-glass, rayon, nylon, wool, cotton etc. Layer Y could, for example, be lightly attached to layer X by a water-soluble adhesive.

Advantages of the structures described herewithin are applicable also to veterinary adaptation. In the illustration of the cat subject 30 of FIG. 12, the composite cast comprising sections 12 and 14 fastened at closed position by tape components 18 is similar to those set forth herein for human usage.

Although a less-preferred embodiment, an adaptation of conventional or modified plaster cast materials and procedures to structures and methods of the invention is conceivable within the scope thereof. Thus, for example, in FIGS. 1 and 2 the completed cast sections 12 and 14 could be considered as composed of a sheet-like support material upon which is formed one or more layers of hardened plaster of paris. Similarly, in FIG. 5 the sections 12a and 14 a could be regarded as embodying plaster of paris in a ductile or paste-like condition. The examples of FIGS. 7–9 and 13 might also be so regarded, utilizing a reinforcing means such as component 34a of FIG. 10. Use of plaster of paris would require extreme care in retaining it within the sections.

It is contemplated that the joined cast-producing sections 12a and 14a are to be provided in a range of widths and lengths to meet requirements of various basic body members and sizes thereof, e.g., the neck, upper arm, fore-arm, wrist, thigh, calf, ankle etc. As shown in FIG. 6, the material can be trimmed after its application to the appendage. Alternatively, the appendage circumference can be measured in advance with a tape-measure and the appropriate length of the two joined sections predetermined and provided. The joining line (a) as shown in FIGS. 1-7 is carefully chosen with respect to its location on the appendage for ease of opening and closing the sections 12 and 14 and when opened exposing the area to be treated. The addition of padding or other layer components as suggested in FIG. 11 needs to be considered in determining correct length of joined sections 12a and 14a.

While an adhesive tape of special strength and flexibility characteristics has been specified for hinge and closure purposes, as at 16 and 18 of FIG. 7, laterally rigid means such as a lightweight metallic hinge and latch may be employed, attached to the sections 12 and 14 by pin means, epoxy resin or any other suitable means. Wherein fiberglass has been specified in examples of structure supra, other materials in filament form are of possible usage, such as polypropylene, polyethylene, nylon, rayon etc.

It will be understood that the subject invention may be practiced in other ways without departing from the character or spirit thereof. The preferred embodiments described herein are to be regarded, therefore as illustrative and not restrictive, the scope thereof being indicated by the appended claims, and all variations which come within the meaning of the claims are intended to be embraced therein.

What is claimed is:

1. An orthopedic device or assemblage adapted to rapidly form a cast composed of pivotally interconnected individually movable sections for providing at closed position immobilization and repair of a displaced, fractured or otherwise injured body member or area while permitting at open position direct visual and tactile access to said member or area at all times for inspection and treatment purposes and avoiding cutting of the cast to obtain its removal or in most cases avoiding the need to effect its complete removal during treatment, comprising: a first preferably generally-rectangular cast-producing section composed of a flexible supportive sheet material adapted to be superimposed with and generally conform to the contours of a given impaired area of said body member; a second cast-producing section substantially similar to said first section adapted to be superimposed with and conform to the contours of an impaired area of said body member contiguous said first-named area; a substance impregnated throughout both said sections of sheet material adapted to operate therewith in forming a cast; pivotal hinge means adapted to so interconnect and dispose said first and second sections of sheet material along contiguous margins therof as to permit manually induced pivotal turning movement of said sections toward and away from one another; means enabling provision of a liquid cooperating with said sheet material and impregnated substance in forming said cast; and means for releasably holding said first and second sections at functional closed position superposed with said body member or area after formation of said cast.

2. A device as defined in claim 1 wherein said material is a cloth-like sheet material.

3. A device as defined in claim 1 wherein said supportive sheet material is a multi-layer material including integral reinforcing means.

4. A device as defined in claim 1 wherein said means for holding said sections at closed position is a strong flexible adhesive tape.

5. A device as defined in claim 1 wherein at least one of said sections includes a laterally rigid component extending longitudinally of the body member enclosed by the joined sections.

6. A device as defined in claim 1 further including a removable preferably elastomeric sheet material insertable between said sections and said body member to serve as a barrier to said liquid.

7. A device as defined in claim 1 wherein said impregnated substance is a polyurethane prepolymer activated by exposure to water and wherein said liquid is water.

8. A device as defined in claim 7 wherein said polyurethane is non-foamable.

9. A device as defined in claim 1 wherein said supportive sheet material of said sections comprises at least one layer of fiberglass.

10. A device as defined in claim 9 wherein said layer of fiberglass is knitted.

11. A device as defined in claim 1 wherein said supportive sheet material is a multi-layer material.

12. A device as defined in claim 11 wherein said supportive sheet material is porous and the pores thereof are substantially aligned.

13. An orthopedic device or assemblage for forming a cast composed of individually pivotally interconnected movable sections for providing at closed position immobilization of a displaced, fractured or otherwise impaired body member while permitting at open position direct visual and tactile access to said member for inspection and treatment purposes and avoiding cutting of the cast to effect such access or its ultimate removal comprising: a first cast-producing section composed of a pliant, liquid absorptive, supportive sheet-material adapted to be wrapped around and generally conform to contours of such body member; a second cast-producing section substantially similar to said first section adapted to be wrapped around and generally conform to contours of a portion of such body member contiguous with said first-mentioned contours; a substance impregnated substantially throughout said first and second sections of sheet material adapted to harden the material of said sections to form a cast when a liquid of given characteristics is imbibed into said sections; interconnecting hinge means adjoining adjacent edges or margins of said sections to enable manually induced hinged movement of the completed hardened cast sections toward and away from such body member and one another; and means for releasably holding said first and second sections at functional closed position embracing such body member.

14. A prefabricated assembly for use in preparing an orthopedic cast for a body member comprising:
first and second generally sheet-like cast-producing sections of a material which is sufficiently flexible to be conformable to the contours of a body member, said cast-producing sections comprising a composition impregnated or otherwise incorporated therein, which composition is treatable by the application of a curing agency to convert the relatively flexible material of said sections into a relatively rigid material, and hinge means firmly joining contiguous margins of said respective sections to enable hinged movement of each of said sections relative to the other, whereby, prior to the application of such curing agency, the said sections of said assembly may be wrapped about a body member and conformed to the contours thereof, and, after being converted by the application of such a curing agency into a relatively rigid material to form a cast for such body member, the said sections of said assembly may be moved relative to each other about said hinge means for access to such body member.

* * * * *